United States Patent
Mathis et al.

(10) Patent No.: US 7,309,567 B1
(45) Date of Patent: Dec. 18, 2007

(54) METHOD FOR REDUCING FLUORESCENCE QUENCHING IN BIOASSAYS

(75) Inventors: Gerard Mathis, Bagnols sur Ceze (FR); Herve Bazin, Villeneuve les Avignon (FR); Eric Trinquet, Pont Saint Esprit (FR)

(73) Assignee: CIS Bio International, Saclay (FR)

( * ) Notice: Subject to any disclaimer, the term of this patent is extended or adjusted under 35 U.S.C. 154(b) by 0 days.

(21) Appl. No.: 09/936,563

(22) PCT Filed: Mar. 14, 2000

(86) PCT No.: PCT/FR00/00608

§ 371 (c)(1),
(2), (4) Date: Sep. 14, 2001

(87) PCT Pub. No.: WO00/55630

PCT Pub. Date: Sep. 21, 2000

(30) Foreign Application Priority Data

Mar. 15, 1999 (FR) .................................. 99 03150

(51) Int. Cl.
*C12Q 1/64* (2006.01)
*C07H 21/04* (2006.01)
*C12N 11/00* (2006.01)
*C12N 9/99* (2006.01)
*G01N 33/533* (2006.01)

(52) U.S. Cl. .............................. 435/6; 435/7; 435/174; 435/183; 436/546; 436/800; 514/44; 536/22.1; 534/15; 540/467; 540/469

(58) Field of Classification Search ................ 435/6–7, 435/174, 183, 7.1; 514/44; 536/22.1, 23.1, 536/24.1, 25.3; 534/15; 436/546, 800; 540/465, 540/467, 469
See application file for complete search history.

(56) References Cited

U.S. PATENT DOCUMENTS

| 5,124,246 A | * | 6/1992 | Urdea et al. ................... 435/6 |
| 5,162,508 A | * | 11/1992 | Lehn et al. .................... 534/15 |
| 5,457,185 A | * | 10/1995 | Lehn et al. .................... 534/15 |
| 5,534,622 A | * | 7/1996 | Lehn et al. .................... 534/15 |
| 5,559,207 A | * | 9/1996 | Sessler et al. .............. 530/300 |
| 5,985,563 A | * | 11/1999 | Hyldig-Nielsen et al. ...... 435/6 |
| 6,306,975 B1 | * | 10/2001 | Zhao et al. ................. 525/276 |
| 6,340,747 B1 | * | 1/2002 | Bazin et al. ............... 536/23.1 |

OTHER PUBLICATIONS

Li et al, "Amine-Reactive Forms . . . Energy Transfer Measurements", 1997, Bioconjugate Chem., vol. 8, pp. 127-132.*

* cited by examiner

*Primary Examiner*—Kenneth R. Horlick
*Assistant Examiner*—Joyce Tung
(74) *Attorney, Agent, or Firm*—Millen, White, Zelano, Branigan, P.C.

(57) ABSTRACT

The invention relates to a process for reducing the fluorescence quenching caused by the measuring medium, in a fluorescence assay for an analyte using at least one fluorescent label, characterized in that a fluorescent conjugate comprising an oligonucleotide bonded to a rare-earth metal cryptate is introduced into the measuring medium.

51 Claims, 1 Drawing Sheet

Conjugate KH-ODN1

Figure 1:
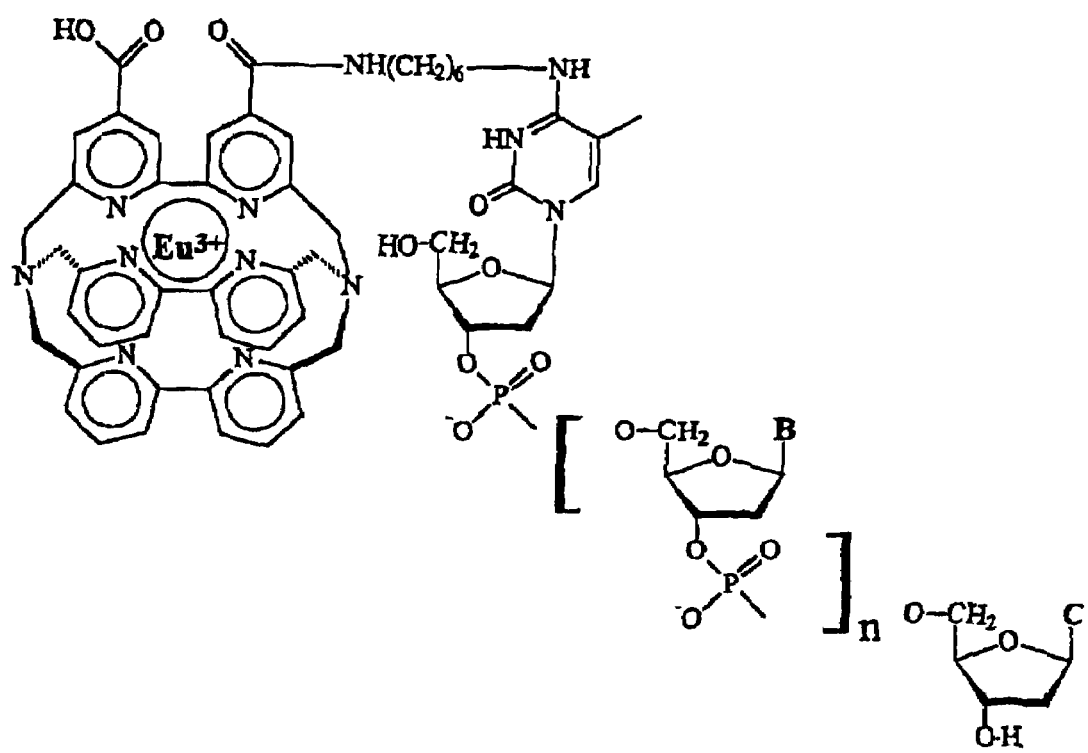

B = Adenine (A), Guanine (G), Cytosine (C), Thymine (T)

C = Cytosine

METHOD FOR REDUCING FLUORESCENCE QUENCHING IN BIOASSAYS

The invention relates to the use of a fluorescent conjugate comprising an oligonucleotide bonded to a rare-earth metal cryptate, for reducing the fluorescence quenching caused by the measuring medium, in a fluorescence assay for an analyte using at least one fluorescent label.

The advancement of knowledge in biology is creating an increasing need for diagnostic methods enabling biomolecules to be monitored or quantified.

At the same time, there is a disaffection toward the radioactive labels which are generally involved in reference assay methods. In general, efforts are currently directed towards replacing radioactive tracers with other labels and mainly with fluorescent labels. The use of fluorescent labels under ideal conditions makes it possible to obtain high sensitivities which are theoretically equivalent to those obtained with radioactive tracers.

In practice, the performance qualities of fluorescent tracers are limited firstly by the presence of a background noise which is often high and, secondly, by the fact that they are generally very sensitive to changes in their environment. Small changes in the pH, the polarity, the presence of dissolved oxygen or the proximity of heavy atoms (iodine for example) or absorbing groups can modify their quantum yield (in the sense of an enhancement or a quenching) or shift the emission wavelength.

It is known that the interaction with proteins present in the serum often causes a quenching of the fluorescence.

The problems inherent to the methods of analysis by measuring fluorescence are listed in a review article (I. Hemmilä, Clin. Chem. 31/3, 359-370 (1985)).

The problems inherent to the background noise arising from the intrinsic fluorescence of proteins and also of other biomolecules present in biological samples may be solved by using fluorescent labels formed from complexes of rare-earth metals (mainly europium) which allow a temporal selection of the specific signal. The particularly long lifetimes (0.1 ms to 1 ms approximately) which characterize europium complexes make it possible, by means of a resolved-time measurement, to be free of the background noise arising, for example, from the serum proteins, this noise being characterized by a relatively short lifetime (about 4 ns).

Indirect labeling of nucleic acids with a trisbipyridine europium [TBP-($Eu^{3+}$)] cryptate (cryptate described in patent EP 0321353) has been carried out using an anti-DNP antibody labeled with this cryptate, the dinitrophenyl (DNP) group being introduced at the 5' end of synthetic oligonucleotides (E. Lopez et al., Clin. Chem. 39/2, 196-201 (1993)).

The use of antibodies labeled using a TBP-($Eu^{3+}$) cryptate has, moreover, been extended to the field of immunodiagnostics. The use of a cryptate as a marker has made it possible to develop homogeneous-type immunoassays based on a resolved-time measurement of fluorescence associated with a non-radiative energy transfer (G. Mathis et al., Clin. Chem., 39, 1251 (1993)).

A format of homogeneous type has the considerable advantage of allowing real-time monitoring of the kinetics of formation of an immunological complex, but does not, however, make it possible to be free of any unfavorable interactions between the label and the molecules present in a biological medium (quenching of the fluorescence).

A restoration of the photophysical properties, and in particular the lifetime, may be obtained in a serum medium by adding fluoride ions to the medium, as described in application WO 92/01224.

It has now been found that conjugating a rare-earth metal cryptate molecule to an oligonucleotide chain makes it possible to obtain a cryptate-oligonucleotide fluorescent conjugate which has novel and unexpected photophysical properties.

Said conjugate has the advantageous property of being less sensitive, compared to cryptate alone, to the phenomenon of fluorescence quenching resulting from an interaction with molecules present in the medium.

This observation is of great interest since it enables fluorescence measurements to be performed in biological media without using an adjuvant such as fluoride ions.

The cryptate-olignucleotide conjugates therefore constitute novel labels, which may be coupled to a biological molecule having a recognition role and which can bind to a partner.

The cryptate-oligonucleotide conjugate coupled to a receptor, such as an antibody or streptavidin, keeps its photophysical properties (resistance to quenching) and has advantageous properties compared to cryptate-antibody or cryptate-streptavidin conjugates.

According to a first aspect, the invention therefore relates to a process for reducing the fluorescence quenching caused by the measuring medium, in a fluorescence assay for an analyte using at least one fluorescent label, characterized in that a fluorescent conjugate comprising an oligonucleotide bonded to a rare-earth metal cryptate is introduced into the measuring medium.

In an advantageous aspect, the fluorescent conjugate is, itself, used as the only label or as one of the fluorescent labels in the assay.

In the present description, the term "analyte" is intended to mean any substance or group of substances, and also the analogs thereof, which it is desired to detect and/or to determine.

The process as claimed in the invention finds an important application in processes for homogeneous phase assaying "by competition" or "by excess".

In the remainder of the description, the notion of "cryptate" and also the nomenclature for the macrocycles and polycycles which may be used are as defined by J. M. Lehn in Struct. Bonding (Berlin), 16, 1, 1973 and in Acc. Chem. Res. 11, 49, (1978).

In the present description, the term "oligonucleotide" is intended to mean:

either a chain of ribonucleotide or deoxyribonucleotide units bonded to one another via phosphodiester-type bonds;

or a chain of ribonucleotide or deoxyribonucleotide units or of analogous units of nucleotides modified on the sugar or on the base and bonded to one another via natural phosphodiester-type internucleotide bonds, some of the internucleotide bonds optionally being replaced with phosphonate, phosphoramide or phosphorothioate bonds. These various oligonucleotide families are described in Goodchild, *Bioconjugate Chemistry*, 1(3), May/June 1990, 77-99;

or a chain comprising both ribonucleotides or deoxyribonucleotide units bonded to one another via phosphodiester-type bonds and analogous units of nucleosides bonded to one another via amide bonds, commonly termed "PNAs" (peptide nucleic acids), as described in M. Egholm et al., J. Am. Chem. Soc., 1992, 114, 1895-1897; such compounds are, for example, described in R. Vinayak et al., Nucleoside & Nucleotide, 1997, 16 (7-9), 1653-1656.

The use of each of these types of oligonucleotide constitutes an advantageous aspect of the invention.

The term nucleotide "analog" or nucleoside "analog" is intended to mean a nucleotide/nucleoside comprising at least one modification relating to the sugar or the nucleobase, or a combination of these modifications. By way of example, mention may be made of the following modifications:

I. Modifications Relating to the Sugar (Nucleotide or Nucleoside Analogs):

1°) The sugar component may be modified in that the configuration of the hydroxyls (free or involved in a phosphate bridge) is different from the natural configuration (which is, respectively, β-D-erythro in a DNA series and β-D-ribo in an RNA series), such as, for example, in the analogs with the backbone β-D-arabino-pentofuranoside or β-D-xylo-pentofuranoside.

2°) The structure may be modified in that the internucleotide bonds are of the 2'→5' type, such as in the case of the β-D-ribo-pentofuranoside-2'-phosphate or 3'-deoxy-β-D-erythro-pentofuranoside-2'-phosphate derivatives.

Nucleotides exist in which the structure includes the two modifications above, such as β-D-xylo-pentofuranoside-2'-phosphate.

3°) The structure may differ from the natural model in that the 4' carbon has an opposite configuration, which is the case for α-L-threo-pentofuranoside-3'-phosphate. The difference may relate to the configuration of the carbon in 1' (anomeric position), which is the case for α-D-erythro-pentofuranoside-3'-phosphate. Nucleotides/nucleosides exist in which the structure includes the two modifications above, such as β-L-threo-pentofuranoside-3'-phosphate.

4°) The structure may differ from the natural model in that the oxygen in 4' is replaced with a carbon (carbocylic analog) or with a sulfur, such as 4'-thio-β-D-erythro-pentofuranoside-3'-phosphate.

5°) The structure may differ from the natural model in that one of the hydroxyls of the sugar is alkylated, for example in the backbone 2'-O-alkyl-β-D-ribo-pentofuranoside-3'-phosphate, the alkyl group possibly being a methyl or allyl group, for example.

6°) The structure may differ from the natural model in that only the sugar component is conserved, such as in 1,2-dideoxy-D-erythro-pentofuranose-3-phosphate, or in that the sugar is replaced with a polyol such as propanediol.

II. Modifications Relating to Nucleobase (Nucleotide Analogs):

1°) The nucleobase may be modified in that the substituents of the natural bases are modified, such as in 2,6-diaminopurine, hypoxanthine, 4-thiothymine, 4-thiouracil or 5-ethynyluracil.

2°) The positions of the substituents may be switched in comparison with the natural bases, such as in isoguanosine or isocytosine.

3°) A nitrogen atom of the nucleobase may be replaced with a carbon atom, such as in 7-deazaguanosine or 7-deazaadenine.

Furthermore, as mentioned above, the bonds between the sugar units or the analogs thereof may also be modified, for example by replacing one or more of the oxygen atoms of the natural phosphodiester bond with a carbon (phosphonate series), a nitrogen (phosphoramide series) or a sulfur (phosphorothioates).

Advantageously, the oligonucleotide of the conjugate as claimed in the invention consists of ribonucleotide or deoxyribonucleotide units, one of which may comprise a functional group introduced or generated on said unit, or a functional group introduced using a spacer arm bonded to the terminal phosphate group in the 3' or 5' position.

According to a preferred aspect, said unit is the 5' terminal unit or 3' terminal unit.

The oligonucleotide which may be used according to the invention will preferably comprise a chain of 5 to 50 nucleotides or a chain of 5 to 50 nucleotides and nucleotide or nucleoside analogs as defined above.

According to a particular aspect of the invention, use will be made of an oligonucleotide consisting of a chain of ribonucleotide or deoxyribonucleotide units bonded to one another via phosphodiester-type bonds, and of analogous units of nucleosides bonded to one another via amide bonds, said oligonucleotide comprising at least 5 phosphodiester-type internucleotide bonds at the end intended to be bonded to the cryptate.

According to a preferred aspect, said rare-earth metal cryptate consists of at least one rare-earth metal salt complexed with a macropolycyclic compound of formula

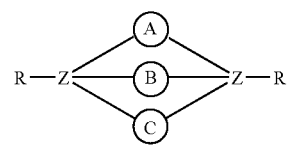

I in which Z is an atom with 3 or 4 valencies, R is nothing or represents hydrogen, a hydroxy group, an amino group or a hydrocarbon-based radical, the divalent radicals Ⓐ, Ⓑ and Ⓒ, are, independently of each other, hydrocarbon-based chains which optionally contain one or more hetero atoms and are optionally interrupted with a hetero macrocycle, at least one of the radicals Ⓐ, Ⓑ and Ⓒ, also comprising at least one molecular unit or consisting essentially of a molecular unit, said molecular unit having a triplet energy which is greater than that of the emission level of the complexed rare-earth metal ion.

In particular, said rare-earth metal cryptate corresponds to formula (I) in which the molecular unit is chosen from phenanthroline, anthracene, benzene, naphthalene, biphenyl and terphenyl, azobenzene, azopyridine, pyridine, bipyridines, bisquinolines and the compounds of the formula below:

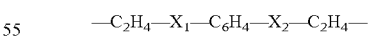

$X_1$ and $X_2$, which may be identical or different, denote oxygen, nitrogen or sulfur,

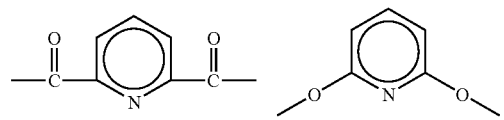

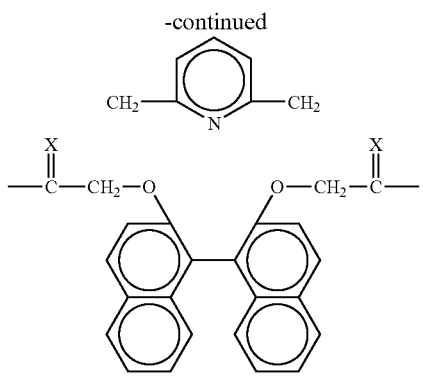

X being oxygen or hydrogen.

Advantageously, said rare-earth metal cryptate consists of a rare-earth metal salt complexed with one of the macrocyclic compounds below:

(22)phenanthroline; (22)phenanthrolinamide; (22)anthracene; (22)anthracenamide; (22)biisoquinoline; (22)biphenylbispyridine; (22)bipyridine; (22)bipyridinamide; the macropolycycles trisbipyridine, trisphenanthroline, phenanthrolinebisbipyridine, biisoquinolinebisbipyridine, bisbipyridine diphenylbipyridine.

Such compounds are, for example, described in patent EP 180 492.

Use may also be made of the macropolycyclic cryptate compounds which complex rare-earth metal ions, in which the molecular unit is chosen from bipyrazines, bipyrimidines and nitrogen-containing heterocycles comprising N-oxide groups.

Macropolycyclic compounds containing bipyrazine units are described in F. Bodar-Houillon et al., New J. Chem., 1996, 20, 1041-1045.

Macropolycyclic compounds containing bipyrimidines are described in J. M. Lehn et al., Helv. Chim. Acta, 1992, 75, 1221, Macropolycyclic compounds comprising nitrogen-containing heterocycles comprising N-oxide groups are described in J. M. Lehn et al., Helv. Chim. Acta, 1991, 74, 572.

In another advantageous aspect, said rare-earth metal cryptate consists of at least one rare-earth metal salt complexed with a macropolycyclic compound corresponding to one of the formulae II or III below:

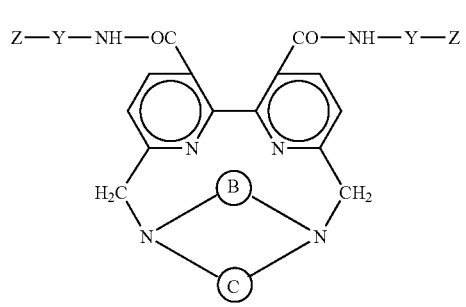

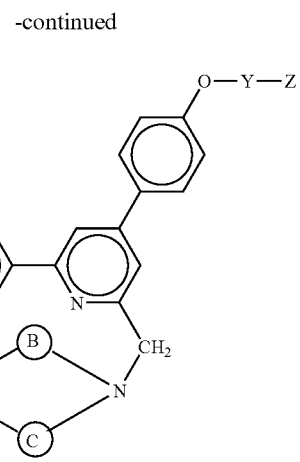

in which:
the ring of formula

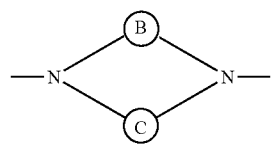

is one of the following rings:

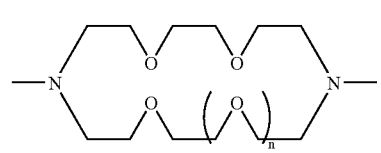

n=0 or 1
[$N_2O_4$] macrocycle or cycle (22)
[$N_2O_3$] macrocycle or cycle (21)

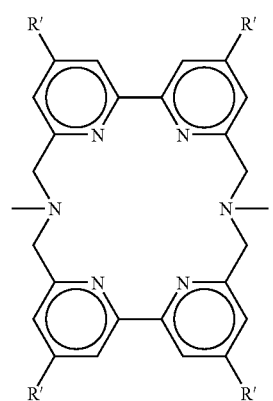

bisbipyridine macrocycle

Y is a spacer group or spacer arm which consists of a divalent organic radical, chosen from linear or branched $C_1$ to $C_{20}$ alkylene groups optionally containing one or more double bonds and/or optionally containing one or more hetero atoms such as oxygen, nitrogen, sulfur or phosphorus or one or more carbamoyl or carboxamido group(s); chosen from $C_5$ to $C_8$ cycloalkylene groups or chosen from $C_6$ to $C_{14}$ arylene groups, said alkylene, cycloalkylene or arylene groups being optionally substituted with alkyl, aryl or sulfonate groups;

Z is a functional group capable of bonding covalently to a biological substance;

R is a methyl group or represents the group —Y—Z;

R' is hydrogen or a group —COOR" in which R" is a $C_1$ to $C_{10}$ alkyl group and preferably represents a methyl, ethyl or tert-butyl group, or alternatively R' is a group —CO—NH—Y—Z.

According to a preferred aspect, the rare-earth metal cryptate of the fluorescent conjugate used according to the invention is a europium cryptate.

In an advantageous aspect, said rare-earth metal cryptate is the europium cryptate Eu trisbipyridine or Eu [bisdiethoxybipyridine.bipyridine].

The rare-earth metal cryptate is preferably bonded covalently to the oligonucleotide either directly or via a spacer arm.

The term "direct bonding" is intended to mean the bonding of the fluorescent label to a functional group which has been introduced onto or generated, beforehand, on one or more atoms of a base or of a pentofuranose unit of the oligonucleotide.

In the present description, the term "functional group" denotes any function which is borne by the nucleotide component or introduced onto this component by any means known to those skilled in the art, and which is capable of bonding, by covalent bonding, directly or after activation, to a function present on the cryptate or on the spacer arm borne by the cryptate. Such functional groups are in particular the $NH_2$, COOH, CHO, OH or SH functions and also the functions capable of providing covalent bonds by substitution (halides, sulfonates, epoxide) or by addition (double bonds of the maleimide type). These functions are generally borne by a hydrocarbon-based chain which is, itself, bonded to the nucleotide component.

Methods for introducing these functional groups are in particular described in C. Kessler, Nonisotopic probing, Blotting and Sequencing, 2$^{nd}$ edition, L. J. Kricka (1995), Ed. Academic Press Ltd., London, p. 66-72. According to a preferred aspect of the invention, the rare-earth metal cryptate is bonded to the oligonucleotide via a spacer arm. The term "spacer arm" is intended to mean any means for covalently attaching the oligonucleotide to the cryptate via a terminal phosphate, via an atom of a purine or pyrimidine base or via an atom of the sugar.

In an advantageous aspect, said spacer arm consists of a divalent organic radical chosen from $C_1$-$C_{20}$ linear or branched alkylene groups optionally containing one or more double bonds or triple bonds and/or optionally containing one or more hetero atoms, such as oxygen, nitrogen, sulfur, phosphorus or one or more carbamoyl or carboxamido group(s); $C_5$-$C_8$ cycloalkylene groups and $C_6$-$C_{14}$ arylene groups, said alkylene, cycloalkylene or arylene groups being optionally substituted with alkyl, aryl or sulfonate groups.

In particular, the spacer arm is chosen from the groups of formulae:

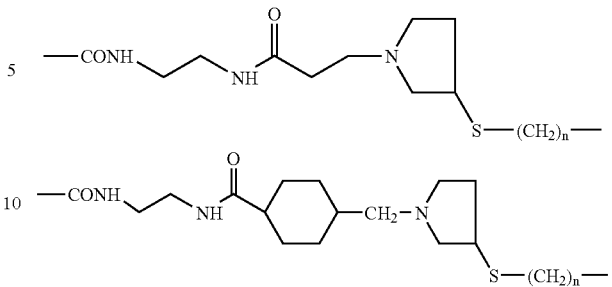

in which n=2 to 6, and —CONH—$(CH_2)_6$—, the attachment via the group —CONH taking place on the cryptate.

According to a further aspect of the invention, the fluorescent conjugate is bonded covalently to one of the members of a pair of molecules capable of binding specifically to one another, such as for example and antigen/antibody pair, a ligand/cellular receptor pair, a biotin/avidin pair, or a pair consisting of a nucleic acid (in particular a single-stranded or double-stranded RNA or DNA, or a single-stranded or double-stranded oligonucleotide) and the nucleic acid comprising the bases complementary thereto.

According to one aspect of the process as claimed in the invention, the fluorescence of the fluorescent conjugate used as a label is emitted directly by the fluorescent label, after excitation at a given wavelength.

According to another aspect of the process as claimed in the invention, another fluorescent label, besides said fluorescent conjugate, is used in the assay. In this case, the fluorescence measured in the assay is emitted indirectly by a nonradiative energy transfer between the conjugate after excitation, termed "donor compound", and another fluorescent molecule, termed "acceptor compound".

In this particular case, the following conditions are satisfied:

firstly, the acceptor fluorescent compound has an absorption spectrum which covers at least partially the emission spectrum of the donor and has a high molar absorbance in this covering range, and an emission spectrum which is in a wavelength range in which the donor exhibits low intrinsic emission;

secondly, the acceptor and the donor are close to one another, the orientation of their transition dipoles being approximately parallel.

The principle of the technique of non-radiative energy transfer is described in particular in G. Mathis et al., Clin. Chem., 1993, 39, 1953-1959.

The rare-earth metal cryptate bonded to the oligonucleotide in the conjugate, which is the donor fluorescent compound, may, in this case, be a europium cryptate, and the acceptor fluorescent compound may, for example, be chosen from allophycocyanin, allophycocyanin B, C-phycocyanin or R-phycocyanin.

The invention is illustrated using the examples below, in which the following abbreviations will be used:

BSA: bovine serum albumin

DTT: dithiothreitol

SMCC: N-hydroxysuccinimide ester of 4-(N-maleimidomethyl)cyclohexane-1-carboxylic acid SMP: N-hydroxysuccinimide ester of 3-maleimidopropionic acid SPDP: N-succinimidyl-3-(2-pyridyldithio)propionate
NBFCS newborn fetal calf serum
TEAB: triethylammonium bicarbonate
TEA Ac: triethylammonium acetate containing 10% acetonitrile
TCEP: tris(2-carboxyethyl)phosphine.

EXAMPLE 1

Photophysical Properties of a Free Cryptate [TBP-(Eu3+)] in the Presence of Serum Method A: The fluorescence spectra and the lifetimes are measured on a Perkin-Elmer spectrofluorimeter of the LS50 type.

A stock solution ($9 \times 10^{-6}$ M concentration in 100 nM phosphate buffer, pH 7) of cryptate [TBP-(Eu3+)]-diamine (purified by RP-HPLC on a C-18 column with a linear gradient of acetonitrile in water containing 1% trifluoroacetic acid and then dried under vacuum), prepared by reacting ethylenediamine on the cryptate [(bisbpy)-(bpy-dimethylester)] described in example 4, section A of application EP 0 321 353, is prepared. In the following examples, this cryptate [TBP-(Eu3+)]-diamine will be abbreviated to K—NH2.

1°) 200 µl of this stock solution is diluted in 400 µl of 100 mM phosphate buffer, pH 7 and the flourescence spectrum (td=0.1 ms, tg=0.4 ms, λexcitation=306 nm, λemission=540 to 750 nm, excitation/emission slits=10/5, yellow filter at emission) and the lifetime t (td=0.1 to 0.6 ms, tg=0.4 ms, λexcitation=306 nm, λemission=620 nm, excitation/emission slits=10/5, yellow filter at emission) are measured:

It is observed that the main line ($\lambda_{em}$=616 nm) has a lifetime in the phosphate buffer of $t_r$=0.60 ms (Correlation Coefficient C.C=0.999).

2°) 200 µl of this stock solution of K—NH2 are diluted in a mixture of 200 µl of 100 mM phosphate buffer, pH 7 and 200 µl of NBFCS, and the spectrum and lifetime are measured under the same conditions.

It is observed that the main line ($\lambda_{em}$=616 nm) has a lifetime in the phosphate buffer of $t_S$=0.15 ms (C.C=0.991).

The quenching factor is given by the expression Q=100-100($t_S$,$t_P$), namely Q=100-100(0.15/0.60)=75, namely 75% quenching.

Method B

A stock solution of cryptate [TBP-(Eu3+)]-diamine in 100 mM phosphate buffer at a concentration of $1.8 \times 10^{-8}$ M is prepared.

The wells of a black-bottomed microplate (96-well HTRF plate, Packard) are filled according to the following protocol:

Condition 1: 100 µl of stock solution of cryptate are mixed with 100 µl of 100 mM phosphate buffer, pH 7 and 100 µl of 100 mM phosphate buffer, pH 7, containing 0.15 M NaCl and 0.1% BSA; the measurements are performed in duplicate. This medium constitutes a reference.

Condition 2: 100 µl of stock solution of cryptate are mixed with 100 µl of NBFCS and 200 µl of 100 mM phosphate buffer, pH 7, containing 0.15 M NaCl and 0.1% BSA (measurement in duplicate).

Resolved-time measurement of the fluorescence is performed on a DISCOVERY machine (Packard) using a laser excitation at 337 nm and an acquisition window of 50 µs to 400 µs.

In the phosphate buffer alone (condition 1), it is observed that the intensity of the emission at 620 nm is $1.41 \times 10^5$ afu (arbitrary fluorescence units). In the adjacent wells of the same microplate, the solutions containing serum (condition 2) exhibit an intensity of the emission at 620 nm of $2.9 \times 10^4$ afu.

The decrease in the intensity of the signal at 620 nm in the presence of serum compared to the reference in the phosphate buffer makes it possible to demonstrate the phenomenon of quenching caused by the serum.

$$100-100[E_{620}(\text{serum})/E_{620}(\text{ref})]=100-100(2.9 \times 10^4/1.41 \times 10^5)=80\%$$

This method allows an overall estimation of the decrease in the signal which comes either from a decrease in the lifetime or from a decrease in the emission at 620 nm.

It makes it possible to work at lower concentrations compared to method A and allows simultaneous measurement of several samples by carrying out the procedure under conditions which are as close as possible to those encountered in an immunoassay.

EXAMPLE 2

Synthesis and Purification of an Oligodeoxynucleotide-Cryptate [TBP-(Eu3+)]

1°) Synthesis of an oligodeoxynucleotide functionalized with an aminohexyl arm (AH-ODN1):

An oligodeoxynucleotide (ODN) of sequence 5' $^{AH}$C ACG CCA CTA GCT CC-3' modified in its 5' end with an aminohexyl (AH) arm is synthesized on a solid support via the phosphite-phosphoramidite method using a DNA synthesizer (Applied Biosystems type 392) according to the manufacturer's protocol. A modified nucleotide is introduced in 5' by coupling an N,N-diisopropyl-β-cyanoethyl-phosphoramidite obtained from 5'-O-(4,4'-dimethoxytrityl)-N-4-(6-trifluoroacetamidohexyl)-2'-deoxycytidine prepared by trifluoroacetylation of 5'-O-(4,4'-dimethoxytrityl)-N-4-(6-aminohexyl)-2'-deoxycytidine as described in Roget et al. Nucleic Acids Res., 17, 7643-7650, (1989).

After synthesis on a DNA synthesizer (Applied Biosystem 392) in the "trityl-on" mode following the corresponding user guide, the oligonucleotide is treated with concentrated aqueous ammonia (16 h at 55° C.) and purified by HPLC on an LiChrospher® RP-18E 250-10 column (10 µm) (Merck, Darmstat, Germany) with a gradient of acetonitrile in 50 mM triethylammonium acetate (buffer A: 5% acetonitrile, buffer B: 50% acetonitrile; flow rate 5 ml/min, gradient of 10% B to 60% B in 20 min, 60% B isocratic gradient for 5 min, and then gradient of 60% B to 1-100% B in 5 min), according to the method described in Oligonucleotide synthesis: A practical approach. Ed M. J. Gait. IRL Press, Oxford. The fractions corresponding to a major peak (retention time greater than 20 min) are evaporated. After evaporation and co-evaporation with water, the partially deprotected oligonucleotide thus obtained is detritylated with 80% acetic acid (room temperature, 30 min), then, after evaporation and coevaporation, the completely deprotected oligonucleotide is taken up in 50 µl of 100 mM triethylammonium bicarbonate (TEAB), pH 8, and precipitated with 1.5 ml of n-butanol. After centrifugation, the supernatant is discarded and the precipitate dried under vacuum is taken up with 200 µl of water. This stock solution (oligonucleotide termed AH-ODN1) has an absorption of 37 $AU_{260}$/ml.

2°) Coupling of a molecule of cryptate [TBP-(Eu3+)] to an oligodeoxynucleotide functionalized with an aminohexyl arm (AH-ODN1):

An aliquot portion (150 µl) of the stock solution of the oligonucleotide obtained above (5.5 $AU_{260}$, i.e. about 39 nmol) is diluted with 150 µl of a 0.1 M aqueous TEAB solution, pH 7.8, and 60 µl of a solution of activated cryptate [TBP-(Eu3+)] (4 mg/ml), i.e. 171 nmol (about 4 equivalents) are added. The activated (N-hydroxysuccinimide/dicyclohexylcarbodiimide) cryptate [TBP-(Eu3+)] is prepared extemporaneously from [(bisbipy)-(bipy diacid)] europium cryptate, itself obtained from the [(bisbipy)-(bipy dimethyl ester)] europium cryptate described in example 4, section A of application EP 0 321 353.

After 30 min with stirring, 15 µl of 1 M TEAB, pH 8.5, are added, followed by evaporation under vacuum (speed-vac) until a volume of 200 µl is obtained, this is loaded onto an NAP10 column (Pharmacia) equilibrated in 25 mM TEAAc buffer, pH 7, containing 10% acetonitrile, elution is then carried out with the same buffer according to the manufacturer's protocol, the fraction excluded is collected in a volume of 1 ml and this fraction is concentrated (speed-vac) until a volume of 200 µl is obtained.

3°) Purification of a conjugate formed from a cryptate [TBP-(Eu3+)] and from an oligodeoxynucleotide functionalized with an aminohexyl arm (conjugate KH-ODN1):

The conjugate KH-ODN1 is analyzed by FPLC on a mono-Q column (Pharmacia) using the following conditions (buffer C: 20 mM sodium acetate, pH 5, containing 10% acetonitrile. Buffer D: 20 mM sodium acetate, pH 5, 1 M lithium chloride containing 10% acetonitrile. Gradient: 0 to 2 min isocratic 20% D, 2 min to 30 min gradient of 20% D to 60% D, flow rate 1 ml/min).

The oligonucleotide AH-ODN1 analyzed by FPLC under the conditions above exhibits a retention time Rt=16.4 min. Under the same conditions, the conjugate KH-ODN1 exhibits a retention time Rt=15.4 min.

The entire excluded fraction from the NAP10 column (200 µl) is then injected onto the mono-Q column, and the fraction corresponding to a retention time of 15 min is collected, concentrated down to 300 µl and desalified on a NAP10 column equilibrated in a 25 mM TEAAc buffer, pH 7, containing 10% acetonitrile. Elution is carried out using the same buffer according to the manufacturer's protocol and the excluded fraction is collected in a volume of 1 ml. This fraction corresponds to the pure conjugate KH-ODN1 and is characterized by an ultraviolet spectrum which exhibits a maximum at 258 nm (ODN component) and a shoulder around 305 nm (cryptate component); the absorbance ratio $A_{260}/A_{305}=4.46$ is close to the theoretical ratio obtained by calculating the ratio of the molar absorbances of the components of the conjugate taken individually $\epsilon_{260}(ODN)+\epsilon_{260}(cryptate)/\epsilon_{305}(cryptate)=(135\,000+19\,000)/30\,000 \approx 5$.

The structure of the conjugate KH-ODN1 is represented in FIG. 1.

4°) Synthesis of a cryptate-oligonucleotide conjugate (K-ODN2)

The synthesis is repeated according to the protocol above, constructing the oligonucleotide sequence GGG GGT TTT TTT TTT ($G_5T_{10}$) in place of ACG CCA CTA GCT CC.

EXAMPLE 3

Photophysical Properties of an Oligonucleotide-Cryptate [TBP-(Eu3+)] Conjugate in the Presence of Serum Method A: The fluorescence spectra and the lifetimes are measured on a Perkin-Elmer spectrofluorimeter of the LS50 type.

The stock solution of oligonucleotide-cryptate [TBP-(Eu3+)] conjugate obtained in example 2 (30) is used, while considering the concentration estimated by measuring absorbance $\epsilon_{260}(conjugate)=\epsilon_{260}(ODN)+\epsilon_{260}(cryptate) \cong (154\,000)$] to be $3.5\times10^{-6}$ M.

1°) 200 µl of this stock solution is diluted either in water or in 400 µl of 100 mM phosphate buffer, pH 7, and the fluorescence spectrum (td=0.1 ms, tg=0.4 ms, λexcitation=306 nm λemission=540 to 750 nm, excitation/emission slits=10/5, yellow filter at emission) and also the lifetime t (td=0.1 to 0.6 ms, tg=0.4 mS, λexcitation=306 nm, λemission=620 nm, excitation/emission slits=10/5, yellow filter at emission) are measured:

In water or in the phosphate buffer, a spectrum profile is observed which is different from that conventionally observed for the cryptate [TBP-(Eu3+)]-diamine: the main line ($\lambda_{em}$=620 nm) has a lifetime of $t_P$=1.1 ms (Correlation Coefficient C.C=0.999).

2°) 200 µl of this stock solution are diluted in a mixture of 200 µl of 100 mM phosphate buffer, pH 7, and of 200 µl of NBFCS and the spectrum and lifetime are measured under the same conditions.

It is observed that the main line ($\lambda_{em}$=620 nm) has a lifetime in the phosphate buffer of $t_S$=1.1 ms (C.C=0.99).

In this case, no extinction by reduction of the lifetime is observed.

Method B:

The stock solution of oligonucleotide-cryptate [TBP-(Eu3+)] conjugate as obtained in example 2 (3°) is used. By measuring absorbance at 260 nm, the concentration is estimated to be $3.5\times10^{-6}$ M. This stock solution is diluted in 100 mM phosphate buffer in order to obtain a final concentration of $2\times10^{-8}$ M.

The wells of a black-bottomed microplate (HTRF 96-well plate, Packard) are filled according to the following protocol:

Condition 1: 100 µl of stock solution of conjugate K-ODN1 are mixed with 100 µl of 100 mM phosphate buffer, pH 7, and 200 µl of 100 mM phosphate buffer, pH 7, containing 0.15 M NaCl and 0.1% BSA; the measurements are carried out in duplicate. This medium constitutes a reference.

Condition 2: 100 µl of stock solution of conjugate K-ODN1 are mixed with 100 µl of NBFCS and 100 µl of 100 mM phosphate buffer, pH 7, containing 0.15 M NaCl and 0.1% BSA (measurement in duplicate).

Resolved-time measurement of the fluorescence is performed on a DISCOVERY machine (Packard) using a laser excitation at 337 nm and an acquisition window of 50 µs to 400 µs.

In the phosphate buffer alone (condition 1), it is observed that the intensity of the emission at 620 nm is $2.8\times10^5$ afu (arbitrary fluorescence units). In the adjacent wells of the same microplate, the solutions containing serum (condition 2) exhibit an intensity of the emission at 620 nm of $2.8\times10^5$ afu.

In this case, no decrease in the intensity of the signal at 620 nm is observed in the presence of serum compared to the reference in the phosphate buffer. There is, therefore, no phenomenon of quenching caused by the serum.

The quenching calculated using the following formula is:

$$100-100[E_{620}(serum)/E_{620}(ref)]=100-100(2.8\times10^5/2.8\times10^5)=0\%$$

EXAMPLE 4

Compared Photophysical Properties of an Oligonucleotide-Cryptate Conjugate and of a Reference Cryptate [TBP-(Eu3+)], in the Presence of Uric Acid This example is used to compare the effect of uric acid on the photophysical properties of various molecules containing a europium cryptate unit.

Identical volumes (100 μl) either of a solution of cryptate-labeled conjugate (about $2 \times 10^{-8}$ M, see example 3B), the evaluation of which is desired, or of a reference cryptate solution (about $2 \times 10^{-8}$ M, see example 1B) are pipetted into a series of wells of a microplate.

In each series of wells, 200 μl of 100 mM phosphate buffer, pH 7, containing 0.15 M NaCl and 0.1% BSA are added to the first well (standard 0) and 200 μl of solutions containing increasing concentrations of uric acid in the same buffer are added to the subsequent wells (in order to obtain, for example, final concentrations of 0, 5, 10, 20, 40 and 80 mg/l of uric acid).

The fluorescence is measured in resolved time on a DISCOVERY machine (Packard) using a laser excitation at 337 nm and an acquisition window of 50 μs to 400 μs.

For each series, the intensity of the emission at 620 nm is measured for the standard 0 and also for each concentration of uric acid. For each concentration, the percentage quenching is evaluated using the following relationship:

$100 - 100[E_{620}(\text{uric acid})/E_{620}(\text{standard } 0)]$

The results are given in table 1.

TABLE 1

| [Uric acid] in mg/l | % quenching at 620 nm | |
|---|---|---|
| | K-NH2 | K-G5T10 |
| 0 | 0 | 0 |
| 1.25 | 47 | 8 |
| 2.5 | 66 | 20 |
| 5 | 79 | 28 |
| 10 | 86 | 30 |
| 20 | 88 | 36 |
| 40 | 89 | 40 |
| 80 | 90 | 46 |

It is observed that the percentage quenching of the reference free cryptate greatly increases as a function of the concentration of uric acid. On the other hand, the percentage quenching of the cryptate-oligonucleotide conjugates is significantly lower even for the highest concentrations of uric acid.

Specifically, at the concentration of 5 mg/ml, the reference cryptate K-NH2 exhibits 79% quenching whereas, under the same conditions, the cryptate-oligonucleotide conjugate K-ODN2 exhibits only 28% quenching.

EXAMPLE 5

Synthesis and Purification of a Cryptate [TBP-(Eu3+)]-aminohexyl-oligonucleotide-maleimide Conjugate Synthesis of an oligonucleotide of sequence $G_5T_{10}$ functionalized in its 5' end with a cryptate and in its 3' end with an arm bearing a maleimide reactive group ($^{5'}$K-AH GGG GGT TTT TTT TT $^{MCC-AH}$C T$_{-3'}$).

The synthesis is carried out using an oligonucleotide bearing two aminohexyl arms, one of which is protected (general structure MMT-NH—(CH$_2$)$_6$-($^{5'}$ODN$_{3'}$)—(CH$_2$)$_6$—NH$_2$), according to the scheme below. MMT-AH GGG GGT TTT TTT TT$^{AH}$CT→MMT-AH GGG GGT TTT TT$^{MCC-AH}$CT→$^{5'}$AH GGG GGT TTT TTT TT$^{MCC-AH}$CT→($^{5'}$-AH GGG GGT TT TTT TTT$^{MCC-AH}$C T$_{-3'}$.)

An oligodeoxynucleotide (ODN) of sequence $^{5'}$MMT-AH GGG GGT TTT TTT TT$^{AH}$C T$_{-3'}$, modified in its 5' end with an aminohexyl (AH) arm in the form in which it is protected with a monomethoxytrityl (MMT) group, is synthesized according to the following process:

The N,N-diisopropyl-β-cyanoethylphosphoramidite derivative of 5'-O-(4,4'-dimethoxytrityl)-N-4-(6-trifluoroacetamidohexyl)-2'-deoxycytidine is coupled to a T column (1 μmol) using a process similar to example 1 (1°), then the synthesis is continued by constructing the sequence GGG GGT TTT TTT TT and, finally, a monomethoxytritylaminohexylphosphoramidite derivative (MMT-C6-amino modifier, Cruachem) is coupled using the "trityl-ON" option of the synthesizer. The oligonucleotide $^{5'}$MMT-AH GGG GGT TTT TTT TT CT is treated with concentrated aqueous ammonia (16 h at 55° C.) and purified by HPLC according to the protocol of example 1 (1°).

The partially deprotected oligonucleotide thus obtained is concentrated (speed-vac) and an aliquot portion (0.24 μmol) is taken up with 100 μl of 0.1 M phosphate buffer, pH 8, and treated with 5 mg of SMCC (15 μmol) in 100 μl of acetonitrile (Sigma). After 40 min with stirring at room temperature, the mixture is concentrated to half its volume (speed-vac) and desalified on an NAP10 column equilibrated in 25 mM TEMC, pH 7, 5% acetonitrile. The excluded fraction (1 ml) containing the oligonucleotide of structure $^{5'}$MMT-AH GGG GGT TTT TTT TT$^{MCC-AH}$CT is evaporated to dryness, the residue is taken up with 1 ml of 80% acetic acid and after 20 min at room temperature, the mixture is concentrated and coevaporated (speed-vac) with water and then taken up in 300 μl of water. At this stage, the detritylated oligonucleotide with the following structure $^{5'}$AH GGG GGT TTT TTT TT$^{MCC-AH}$CT is obtained.

This oligonucleotide (0.175 μmol in 300 μl) is diluted with 300 μl of 0.1 M TEAB, pH 7, and then 450 μl (1.27 nmol, i.e. ≈7 eq.) of a solution of activated cryptate [TBP-(Eu3+)] (4 mg/ml) as described in example 2 are added.

After 30 min of stirring, the mixture is evaporated under vacuum (speed-vac) until a volume of 200 μl is obtained, this is loaded onto an NAP10 column (Pharmacia) equilibrated in a 25 mM TEAAc buffer, pH 7, containing 10% acetonitrile and elution is carried out with the same buffer according to the manufacturer's protocol. The excluded fraction is collected in a volume of 1 ml and concentrated (speed-vac) until a volume of 200 μl is obtained. The excluded fraction contains mainly the labeled oligonucleotide of structure (5'-K-AH GGG GGT TTT TTT TT $^{MCC-AH}$C T$_{-3'}$'); this oligonucleotide is purified by injection onto an HR 10/30 column filled with Sephadex G25 which is eluted with 0.1 M phosphate buffer, pH 7, with a flow rate of 1 ml/min. The fraction eluted between 8 and 11 min is collected. 3 ml are thus obtained of a solution containing 17.5 nmol of the pure oligonucleotide $^{5'}$-K-AH GGG GGT TTT TTT TT $^{MCC-AH}$C T$_{-3'}$, which can be directly used for coupling to the thiol functions of a protein ($A_{260}/A_{305}$ ratio=7).

EXAMPLE 6

Coupling of a Cryptate [TBP-(Eu3+)]-aminohexyl-oligonucleotide-maleimide Conjugate to an Antibody An antibody is functionalized with an SPDP (Pierce), after reduction with DTT, the activated antibody is purified on an HR 10/30 column filled with Sephadex G25 which is eluted with 0.1 M phosphate buffer, pH 7 with a flow rate of 1 ml/min. The fraction containing the activated antibody is combined with a cryptate-oligonucleotide conjugate activated with a maleimide group $^{5'}$-K-AH GGG GGT TTT TTT TT $^{MCC-AH}$C T-$_{3'}$ prepared according to example 5. The reaction mixture is then purified on a Superdex 200 column which is eluted as above and the fraction containing the antibody-oligonucleotide-cryptate conjugate is collected.

EXAMPLE 7

Coupling of a Cryptate [TBP-(Eu3+)]-aminohexyl-oligonucleotide-maleimide Conjugate to Streptavidin The streptavidin is activated as in example 6 and it is then labeled using a cryptate-oligonucleotide conjugate activated with a maleimide group $^{5'}$-K-AH GGG GGT TTT TTT TT $^{MCC-AH}$C T-$_{3'}$ prepared according to example 5.

EXAMPLE 8

Photophysical Properties of a protein-oligonucleotide-cryptate [TBP-(Eu3+)] Conjugate The percentage quenching is evaluated in the presence of uric acid according to the protocol of example 4.

A cryptate [TBP-(Eu3+)]-oligonucleotide-antibody conjugate prepared according to the protocol of example 6 is thus evaluated in comparison with a reference cryptate [TBP-(Eu3+)]-antibody prepared by labeling an antibody using cryptate (activated with SMCC) according to a conventional immunochemistry protocol.

A cryptate [TBP-(Eu3+)]-oligonucleotide-streptavidin conjugate prepared according to example 7 is also evaluated in comparison with a reference cryptate [TBP-(Eu3+)]-streptavidin prepared by labeling streptavidin using cryptate (activated with SMCC) according to a conventional immunochemistry protocol.

The results are given in table 2.

TABLE 2

| | Percentage quenching of the signal from the cryptate trisbipyridine at 620 nm | |
|---|---|---|
| [Uric acid] in mg/l | Anti-prolactin cryptate trisbipyridine conjugate | Anti-prolactin oligonucleotide cryptate trisbipyridine conjugate |
| 0 | 0 | 0 |
| 5 | 46 | 2 |
| 10 | 61 | 9 |
| 20 | 71 | 15 |
| 40 | 82 | 20 |
| 80 | 86 | 28 |

| | Percentage quenching of the signal from the cryptate trisbipyridine at 620 nm | |
|---|---|---|
| [Uric acid] in mg/l | Streptavidin cryptate trisbipyridine conjugate | Streptavidin oligonucleotide cryptate trisbipyridine conjugate |
| 0 | 0 | 0 |
| 5 | 74 | 10 |
| 10 | 88 | 11 |
| 20 | 94 | 18 |
| 40 | 97 | 23 |
| 80 | 97 | 32 |

It is observed that, for the high concentrations of uric acid, the reference cryptate-antibody conjugate exhibits 86% quenching whereas, under the same conditions, the cryptate-oligonucleotide-antibody conjugate, exhibits only 28% quenching. For a neighboring concentration of uric acid of between 5 and 10 mg/ml, the fluorescence of the reference conjugate is attenuated by 50% whereas the compound of the invention exhibits less than 10% quenching.

Similarly, it is observed that, under the conditions of a high concentration of uric acid, the reference cryptate-streptavidin conjugate exhibits 97% quenching whereas the cryptate-olignucleotide-streptavidin conjugate exhibits only 32% quenching.

EXAMPLE 9

Coupling of a Cryptate [TBP-(Eu3+)]-maleimide Conjugate to a Thiol-Oligonucleotide The cryptate [(bisbipy)-(bipy dimethyl ester)] described in example 4, section A of application EP 0 321 353 is treated with ethylenediamine and the resulting cryptate diamine purified by RP-HPLC is then treated with SMCC (Pierce) or SMP (Pierce) so as to introduce a maleimide group. A cryptate-maleimide conjugate is thus obtained. This cryptate-maleimide conjugate, purified on RP-HPLC, is coupled to a thiol-oligonucleotide (ODN4 below).

The oligonucleotide used has the following structure:

ODN3: DMT-O(CH$_2$)$_6$—SS—(CH$_2$)$_6$-p-d(TTT TTT TTT GGG GG$^{AH}$CG)$_{3'}$.

The thiol function is introduced in 5' of the oligonucleotide in the form of a disulfide bridge. This functionalization is introduced at the end in the 5' position of the oligonucleotide via a phosphoramidite (C6-disulfide phosphoramidite, Cruachem Ltd., Glasgow). After ammoniacal deprotection and purification (RP-HPLC), the oligonucleotide is treated with TCEP (Pierce, Rockford, Ill.) in order to free the thiol function.

The oligonucleotide with the following structure is thus obtained:

ODN4: HS—(CH$_2$)$_6$-p-d(TTT TTT TTT GGG GG$^{AH}$CG)$_{3'}$.

15 µl of a solution of ODN3 at 156 AU$_{260}$/ml are added to 85 µl of water, 50 µl of a 1 mg/ml solution of TCEP are added, after 20 min at 20° C. the mixture is loaded onto an NAP 10 column (equilibrated in 25 mM TEAAc, pH 7, 5% acetonitrile), the column is eluted, the exclusion volume (1 ml containing about 9 nmol of ODN4) is collected and concentrated in a speed-vac (down to about 100 µl) and 13 nmol of cryptate-maleimide in 50 µl of water are added. After overnight coupling at 4° C., the mixture is purified on NAP10 (elution as above) and the oligonucleotide-cryptate conjugate is eluted in the exclusion volume (1 ml). The absence of free cryptate is verified by analytical FPLC (HR10/30 column filled with Sepharose G25 (Pharmacia), elution with 10 mM phosphate buffer, pH 7).

The oligonucleotide-cryptate [TBP-Eu$^{3+}$] of structure [bpy.bpy.bpy-Eu$^{3+}$]-S—(CH$_2$)$_6$-p-d(TTT TTT TTT GGG GG$^{AH}$CG)$_{3'}$, which has, close to the 3' end, an aminohexyl arm which allows this conjugate to be bonded to a biomolecule, is thus obtained.

EXAMPLE 10

Photophysical Properties of an Oligonucleotide-Cryptate [TBP-Eu$^{3+}$]) Conjugate Obtained According to Example 9

A. Lifetime:

The lifetime is measured on a dilution, in water, of the cryptate-oligonucleotide conjugate obtained in example 9, using the protocol of example 3 (Method A).

It is observed that, in water or in the phosphate buffer, the main line ($\lambda_{em}$=620 nm) has a lifetime of $t_P$=1.33 ms (Correlation Coefficient C.C=0.999), this long lifetime is to be compared with the value of 1.1 ms (example 3A) obtained for the cryptate-oligonucleotide conjugate, the synthesis of which is described in example 2.

B. Quenching by Uric Acid:

The percentage quenching by uric acid is evaluated as described in example 4 so as to obtain final concentrations of 0, 2.5, 5, 10, 20, 40 and 80 mg/l of uric acid.

A reference sample of free cryptate is treated in the same way.

The results are given in table 3 below:

TABLE 3

| Uric acid (mg/ml) | Free cryptate Quenching at 620 nm (%) | Conjugate of example 9 Quenching at 620 nm (%) |
|---|---|---|
| 0 | 0 | 0 |
| 2.5 | 81 | 32 |
| 5 | 92 | 38 |
| 10 | 97 | 43 |
| 20 | 98 | 46 |
| 40 | 98 | 47 |
| 80 | 98 | 53 |

It is observed that the structure of the cryptate-oligonucleotide conjugate confers a resistance to quenching by uric acid of the same order of that which was observed for the conjugate of example 2.

Similarly, the measurement of the lifetime according to example 3A shows that the main line ($\lambda_{em}$=620 nm) has a lifetime in the phosphate buffer of $t_S$=1.1 Ms (C.C=0.99).

Consequently, the way in which the covalent bond between the cryptate unit and the oligonucleotide is created does not have any substantial effect on the photophysical properties of the conjugates.

EXAMPLE 11

Coupling of a cryptate[bisdiethoxybpy.bpy-(Eu3+)]-maleimide Conjugate to a Thiol-Oligonucleotide In this example, a cryptate made of two 4,4'-diethoxy-2,2'-bipyridine units and of one 4,4'-di(methyl carboxylate)-2,2'-bipyridine unit is used. This cryptate is synthesized according to the process described in application EP 0 321 353, by condensation, in the presence of sodium carbonate in acetonitrile at reflux, of 2 equivalents of 6,6'-dibromomethyl-4,4'-diethoxy-2,2'-bipyridine and 1 equivalent of 6,6'-diaminomethyl-4,4'-di(methyl carboxylate)-2,2'-bipyridine derivative. The cryptate [bisdiethoxybpy.diCOOCH$_3$ bpy] NaBr is thus obtained. This sodium cryptate is then converted to europium cryptate [bisdiethoxybpy.diCOOCH$_3$ bpy-EU$^{3+}$] with EuCl$_3$.6H$_2$O in methanol at reflux. This europium cryptate dimethyl ester is then treated with ethylenediamine (4h at 20° C.) and the resulting europium cryptate diamine [bisdiethoxybpy.(di-NH$_2$(CH$_2$)$_2$—NHCO-bpy)-Eu$^{3+}$] is purified by RP-HPLC.

This cryptate will be used as a reference cryptate and will be termed K'NH2 in example 12 below. It is then treated with SMP (Pierce) in order to introduce a maleimide group. A cryptate [bisdiethoxybpy.bipy-Eu$^{3+}$]-maleimide conjugate is thus obtained. This cryptate-maleimide conjugate, purified on RP-HPLC, is coupled, according to the protocol of example 9, to the thiol-oligonucleotide ODN4 described in that example. An oligonucleotide-[bisdiethoxybpy.bpy-(Eu$^{3+}$)] conjugate is thus obtained. The UV spectrum of this conjugate exhibits a maximum around 260 nm corresponding to the oligonucleotide and 2 shoulders around 305 nm and 337 nm corresponding to the cryptate component.

EXAMPLE 12

Photophysical Properties of the oligonucleotide-cryptate[bisdiethoxybpy.bpy-(Eu3+)] Conjugate Obtained According to Example 11

The lifetime measurements for the oligonucleotide-cryptate [bisdiethoxybpy.bpy-(Eu3+)] conjugate (example 11) in the phosphate buffer are carried out according to the protocol described in the example and using, as a reference cryptate, the compound K'NH2 described in example 11.

The results are given in Table 4 below:

TABLE 4

| Meduim | Oligonucleotide-cryptate[bisdiethoxybpy.bpy-(Eu3+)] conjugate Lifetime (ms) | K'NH2 Lifetime (ms) |
|---|---|---|
| Phosphate | 0.8 | 0.6 |
| Phosphate + serum | 0.8 | 0.2 |

It is observed, therefore, that the reference K'NH2 brought together with serum shows a phenomenon of quenching which causes a significant decrease in the lifetime in comparison with the value observed in the phosphate alone.

It is observed that the oligonucleotide-cryptate[bisdiethoxybpy.bpy-(Eu3+)] conjugate is not affected by the serum.

This example shows that the protective effect of the oligonucleotide component is independent of the structure of the cryptate.

The invention claimed is:

1. A process for constructing a signaling molecule by labeling a biological molecule, which can bind to a targeted partner, said process comprising covalently bonding to a biological molecule a labeling agent, wherein said labeling agent is a fluorescent conjugate comprising an oligonucleotide covalently bonded to a rare-earth metal cryptate, wherein said rare-earth metal cryptate consists of at least one rare-earth metal salt complexed with a macropolycyclic compound of formula I

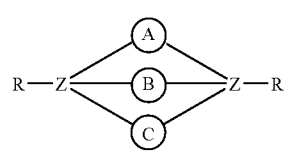

wherein
Z is an atom with 3 or 4 valencies,
R is absence or is hydrogen, a hydroxy group, an amino group or a hydrocarbon-based radical, and
the divalent radicals Ⓐ, Ⓑ and Ⓒ, are each, independently of each other, a hydrocarbon-based chain optionally containing one or more hetero atoms and optionally containing a hetero macrocycle, wherein at least one of the radicals Ⓐ, Ⓑ and Ⓒ, also comprises at least one molecular unit, said molecular unit having a triplet energy which is greater than that of the emission level of the complexed rare-earth metal ion.

2. The process as claimed in claim 1, wherein the oligonucleotide consists of a chain of ribonucleotide or deoxyribonucleotide units bonded to one another via phosphodiester bonds.

3. The process as claimed in claim 1, wherein the oligonucleotide consists of a chain of ribonucleotide or deoxyribonucleotide units or of analogous units of nucleotides modified on the sugar or on the base and bonded to one another via natural phosphodiester internucleotide bonds, wherein some of the internucleotide bonds are optionally replaced with phosphonate, phosphoramide or phosphorothioate bonds.

4. The process as claimed in claim 1, wherein the oligonucleotide consists of a chain comprising both ribonucleotide or deoxyribonucleotide units bonded to one another via phosphodiester bonds and analogous units of nucleosides bonded to one another via amide bonds.

5. The process as claimed in claim 1, wherein the oligonucleotide consists of ribonucleotide or deoxyribonucleotide units, wherein one of said units comprises a functional group selected from $NH_2$, COOH, CHO, OH, SH, halide, sulfonate, epoxide, and maleimide, introduced onto or generated on said one of said units, or the functional group is introduced using a spacer arm bonded to the terminal phosphate group in the 3' or 5' position.

6. The process as claimed in claim 5, wherein said unit is the 5' terminal unit or 3' terminal unit.

7. The process as claimed in claim 1, wherein the oligonucleotide comprises a chain of 5 to 50 nucleotides or a chain of 5 to 50 units containing nucleotides, and nucleotide analogs, nucleoside analogs, or combinations thereof.

8. The process as claimed in claim 1, wherein the oligonucleotide consists of a chain of ribonucleotide or deoxyribonucleotide units bonded to one another via phosphodiester bonds and of analogous units of nucleosides bonded to one another via amide bonds, said oligonucleotide comprising at least 5 phosphodiester internucleotide bonds at the end bonded to the cryptate.

9. The process as claimed in claim 1, wherein the rare-earth metal cryptate is directly bonded covalently to the oligonucleotide.

10. The process as claimed in claim 1, wherein the rare-earth metal cryptate consists of a rare-earth metal salt complexed with one of the macrocyclic or macropolycyclic compounds selected from the following compounds:

2.2.phenanthroline, 2.2.phenanthroline amide, 2.2.anthracene, 2.2.anthracene amide, 2.2.biisoquinoline, 2.2.biphenyl-bis-pyridine, 2.2.bipyridine, 2.2.bipyridine amide, trisbipyridine, trisphenanthroline, phenanthrolinebisbipyridine, biisoquinolinebisbipyridine, bisbipyridine diphenylbipyridine, and macropolycyclic compounds comprising a molecular unit chosen from bipyrazines, bipyrimidines and nitrogen-containing heterocycles comprising N-oxide groups.

11. The process according to claim 1, wherein the rare-earth metal cryptate consists of at least one rare-earth metal salt complexed with a macropolycyclic compound corresponding to one of the formulae II or III below:

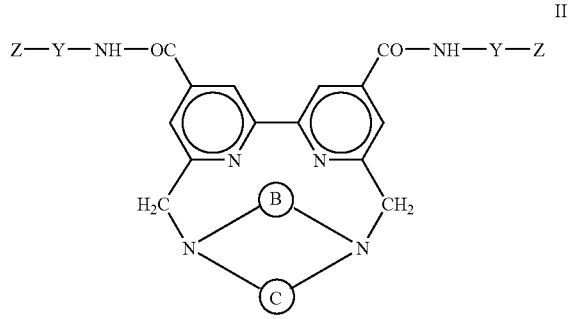

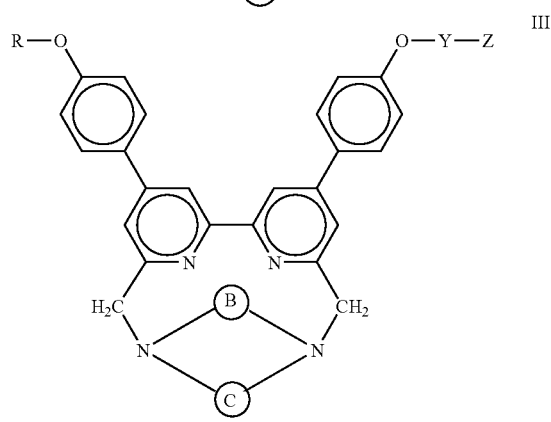

in which:
the ring of formula

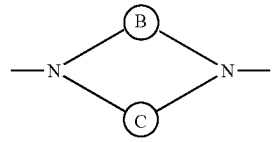

is one of the following rings:

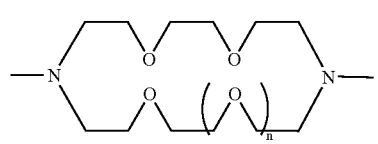

wherein n is 0 or 1,

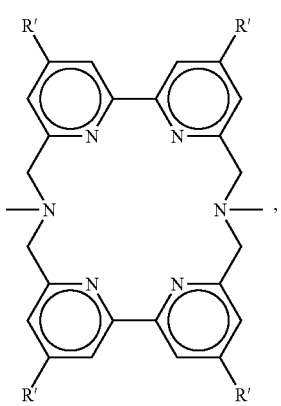

Y is a spacer group or spacer arm which is a divalent organic radical chosen from:
  linear or branched $C_1$ or $C_{20}$ alkylene optionally containing one or more double bonds and/or optionally containing one or more hetero atoms or one or more carbamoyl or carboxamido group(s),
  $C_5$ to $C_8$ cycloalkylene, and
  $C_6$ to $C_{14}$ arylene,
said alkylene, cycloalkylene or arylene are in each case optionally substituted with alkyl, aryl or sulfonate groups;
Z is a functional group capable of bonding covalently to a biological substance;
R is methyl or —Y—Z;
R' is hydrogen, —COOR", or —CO—NH—Y—Z;
R" is $C_1$ to $C_{10}$ alkyl.

12. The process as claimed in claim 1, wherein the rare-earth metal cryptate is bonded to the oligonucleotide via a spacer arm, wherein said spacer arm consists of a divalent organic radical chosen from:
  $C_1$-$C_{20}$ linear or branched alkylene optionally containing one or more double bonds or triple bonds and/or optionally containing one or more hetero atoms or one or more carbamoyl or carboxamino group(s);
  $C_5$-$C_8$ cycloalkylene; and
  $C_6$-$C_{14}$ arylene;
wherein said alkylene, cycloalkylene or aryleneis in each case optionally substituted with alkyl, aryl or sulfonate groups.

13. The process as claimed in claim 12, wherein said spacer arm is:

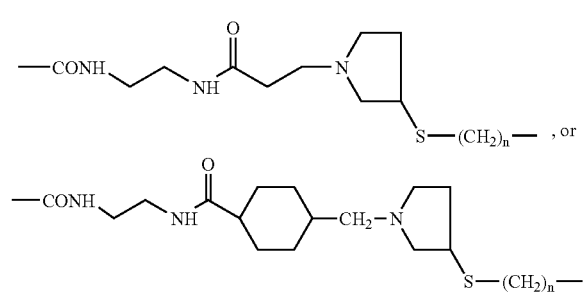

wherein
  n is 2 to 6; or
  the spacer arm is —CONH—$(CH_2)_6$—;
  wherein attachment to the cryptate occurs via the group —CONH.

14. The process as claimed in claim 1, wherein the rare-earth metal cryptate is a europium cryptate.

15. The process as claimed in claim 14, wherein said europium cryptate is Eu trisbipyridine or Eu[bisdiethoxybipyridine.bipyridine].

16. The method as claimed in claim 1, wherein said measuring medium further comprises an acceptor fluorescent compound.

17. A conjugate comprising:
  (1) a rare-earth metal cryptate;
  (2) an oligonucleotide; and
  (3) a biological molecule having a recognition role and which can bind to a partner, wherein said cryptate, oligonucleotide, and biological molecule, are linked by covalent bonds, wherein said rare-earth metal cryptate consists of at least one rare-earth metal salt complexed with a macropolycyclic compound of formula I

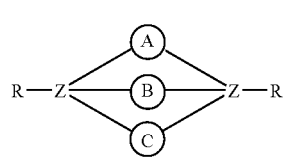

wherein
  Z is an atom with 3 or 4 valencies,
  R is absence or is hydrogen, a hydroxy group, an amino group or a hydrocarbon-based radical, and
  the divalent radicals Ⓐ, Ⓑ and Ⓒ are each, independently of each other, a hydrocarbon-based chain optionally containing one or more hetero atoms and are which optionally contains a hetero macrocycle,
  wherein at least one of the radicals Ⓐ, Ⓑ and Ⓒ also comprises at least one molecular unit, said molecular unit having a triplet energy which is greater than that of the emission level of the complexed rare-earth metal ion.

18. The conjugate according to claim 17, wherein the biological molecule is one member of a pair molecules capable of binding specifically to one another.

19. The conjugate as claimed in claim 17, wherein the oligonucleotide consists of a chain of ribonucleotide or deoxyribonucleotide units bonded to one another via phosphodiester bonds.

20. The conjugate as claimed in claim 17, wherein the oligonucleotide consists of a chain of ribonucleotide or deoxyribonucleotide units or of analogous units of nucleotides modified on the sugar or on the base and bonded to one another via natural phosphodiester internucleotide bonds, wherein some of the internucleotide bonds are optionally replaced with phosphonate, phosphoramide or phosphorothioate bonds.

21. The conjugate as claimed in claim 17, wherein the oligonucleotide consists of a chain comprising both ribonucleotide or deoxyribonucleotide units bonded to one another via phosphodiester bonds and analogous units of nucleosides bonded to one another via amide bonds.

22. The conjugate as claimed in claim 17, wherein the oligonucleotide consists of ribonucleotide or deoxyribonucleotide units, wherein one of said units comprises a functional group selected from $NH_2$, COOH, CHO, OH, SH, halide, sulfonate, epoxide, and maleimide, introduced onto or generated on said one of said units, or the functional group is introduced using a spacer arm bonded to the terminal phosphate group in the 3' or 5' position.

23. The conjugate as claimed in claim 22, wherein said unit is the 5' terminal unit or 3' terminal unit.

24. The conjugate as claimed in claim 17, wherein the oligonucleotide comprises a chain of 5 to 50 nucleotides or a chain of 5 to 50 units containing nucleotides, and nucleotide analogs, nucleoside analogs, or combinations thereof.

25. The conjugate as claimed in claim 17, wherein the oligonucleotide consists of a chain of ribonucleotide or deoxyribonucleotide units bonded to one another via phosphodiester bonds and of analogous units of nucleosides bonded to one another via amide bonds, said oligonucleotide comprising at least 5 phosphodiester internucleotide bonds at the end bonded to the cryptate.

26. The conjugate as claimed in claim 17, wherein the rare-earth metal cryptate is directly bonded covalently to the oligonucleotide.

27. The conjugate as claimed in claim 17, wherein the rare-earth metal cryptate consists of a rare-earth metal salt complexed with one of the macrocyclic or macropolycyclic compounds selected from the following compounds:
2.2.phenanthroline, 2.2.phenanthroline amide, 2.2.anthracene, 2.2.anthracene amide, 2.2.biisoquinoline, 2.2.biphenyl-bis-pyridine, 2.2.bipyridine, 2.2.bipyridine amide, trisbipyridine, trisphenanthroline, phenanthrolinebisbipyridine, biisoquinolinebisbipyridine, bisbipyridine diphenylbipyridine, and macropolycyclic compounds comprising a molecular unit chosen from bipyrazines, bipyrimidines and nitrogen-containing heterocycles comprising N-oxide groups.

28. The conjugate as claimed in claim 17, wherein the rare-earth metal cryptate consists of at least one rare-earth metal salt complexed with a macropolycyclic compound corresponding to one of the formulae II or III below:

II

Z—Y—NH—OC ... CO—NH—Y—Z

III

R—O ... O—Y—Z in which:
the ring of formula is one of the following rings:

1)

wherein n is 0 or 1,

2)

Y is a spacer group or spacer arm which is a divalent organic radical chosen from:
  linear or branched $C_1$ or $C_{20}$ alkylene optionally containing one or more double bonds and/or optionally containing one or more hetero atoms or one or more carbamoyl or carboxamido group(s),
  $C_5$ to $C_8$ cycloalkylene, and
  $C_6$ to $C_{14}$ arylene,
  said alkylene, cycloalkylene or arylene are in each case optionally substituted with alkyl, aryl or sulfonate groups;
Z is a functional group capable of bonding covalently to a biological substance;
R is methyl or —Y—Z;
R' is hydrogen, —COOR", or —CO—NH—Y—Z;
R" is $C_1$ to $C_{10}$ alkyl.

29. The conjugate as claimed in claim 17, wherein the rare-earth metal cryptate is bonded to the oligonucleotide via a spacer arm, wherein said spacer arm is a divalent organic radical chosen from:
$C_1$-$C_{20}$ linear or branched alkylene optionally containing one or more double bonds or triple bonds and/or optionally containing one or more hetero atoms or one or more carbamoyl or carboxamino group(s);
$C_5$-$C_8$ cycloalkylene; and
$C_6$-$C_{14}$ arylene;
wherein said alkylene, cycloalkylene or aryleneis in each case optionally substituted with alkyl, aryl or sulfonate groups.

30. The conjugate as claimed in claim 29, wherein the spacer arm is:

—CONH—CH₂CH₂—NH—CO—CH₂CH₂—N(pyrrolidine)—S—(CH₂)ₙ—, or

—CONH—CH₂CH₂—NH—CO—(cyclohexyl)—CH₂—N(pyrrolidine)—S—(CH₂)ₙ— wherein n is 2 to 6; or
the spacer arm is —CONH—$(CH_2)_6$—;
wherein attachment to the cryptate is via the group —CONH.

31. The conjugate as claimed in claim 17, wherein the rare-earth metal cryptate is a europium cryptate.

32. The conjugate as claimed in claim 31, wherein said europium cryptate is Eu trisbipyridine or Eu [bisdiethoxy-bipyridine.bipyridine].

33. The conjugate as claimed in claim 18, wherein the biological molecule is a cellular receptor, an antigen, an antibody or a nucleic acid.

34. The conjugate as claimed in claim 28, wherein the R" alkyl group is a methyl, ethyl or tert-butyl group.

35. The conjugate as claimed in claim 29, wherein said one or more hetero atoms is oxygen, nitrogen, sulfur, or phosphorus.

36. The process according to claim 11, wherein R" is a methyl, an ethyl or a tert-butyl group.

37. The process according to claim 1, wherein said rare-earth metal cryptate is bonded to said oligonucleotide via a spacer arm, where in said spacer arm is a divalent organic radical chosen from:
a $C_1$-$C_{20}$ linear or branched alkylene optionally containing one or more double bonds or triple bonds and/or optionally containing one or more hetero atoms selected from oxygen, nitrogen, sulfur, and phosphorus or one or more carbamoyl or carboxamino group(s);
a $C_5$-$C_8$ cycloalkylene; and
$C_6$-$C_{14}$ arylene,
wherein in each case said alkylene, cycloalkylene or arylene is optionally substituted by alkyl, aryl or sulfonate groups.

38. The process as claimed in claim 3, wherein the oligonucleotide consists of a chain of ribonucleotide or deoxyribonucleotide units bonded to one another via natural phosphodiester internucleotide bonds, wherein some of the internucleotide bonds are replaced with phosphonate, phosphoramide or phosphorothioate bonds.

39. The process as claimed in claim 1, wherein the rare-earth metal cryptate is bonded covalently to the oligonucleotide via a spacer arm.

40. The process as claimed in claim 1, wherein at least one of the radicals Ⓐ, Ⓑ and Ⓒ consists essentially of a molecular unit having a triplet energy which is greater than that of the emission level of the complexed rare-earth metal ion.

41. The process according to claim 40, wherein
said molecular unit is phenanthroline, anthracene, benzene, naphthalene, biphenyl, terphenyl, azobenzene, azopyridine, pyridine, bypyridine, bisquinoline, —$C_2H_4$—$X_1$—$C_6H_4$—$X_2$—$C_2H_4$—, or $C_2H_4$—$X_1$—$CH_2$—$C_6H_4$—$CH_2$—$X_2$—$C_2H_4$—, and
$X_1$ and $X_2$ are each O, N, or S, or
said molecular unit is

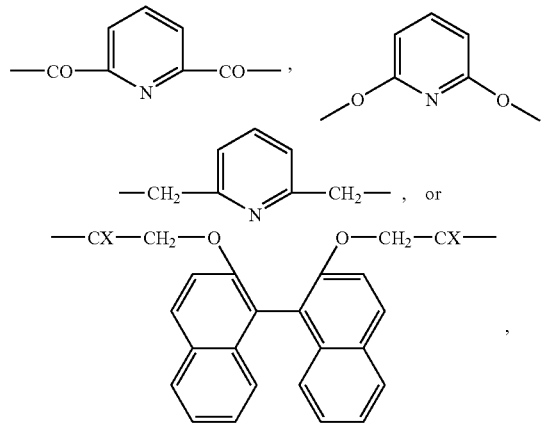

and X is oxygen or hydrogens.

42. The conjugate according to claim 17, wherein said rare-earth metal cryptate is bonded to said oligonucleotide via a spacer arm, where in said spacer arm is a divalent organic radical chosen from:
a $C_1$-$C_{20}$ linear or branched alkylene optionally containing one or more double bonds or triple bonds and/or optionally containing one or more hetero atoms selected from oxygen, nitrogen, sulfur, and phosphorus or one or more carbamoyl or carboxamino group(s);
a $C_5$-$C_8$ cycloalkylene; and
$C_6$-$C_{14}$ arylene,
wherein in each case said alkylene, cycloalkylene or arylene is optionally substituted by alkyl, aryl or sulfonate groups.

43. The conjugate as claimed in claim 20, wherein the oligonucleotide consists of a chain of ribonucleotide or deoxyribonucleotide units bonded to one another via natural phosphodiester internucleotide bonds, wherein some of the internucleotide bonds are replaced with phosphonate, phosphoramide or phosphorothioate bonds.

44. The conjugate as claimed in claim 17, wherein the rare-earth metal cryptate is bonded covalently to the oligonucleotide via a spacer arm.

45. The conjugate as claimed in claim 17, wherein at least one of the radicals Ⓐ, Ⓑ and Ⓒ, consists essentially of a molecular unit having a triplet energy which is greater than that of the emission level of the complexed rare-earth metal ion.

46. The conjugate according to claim 45, wherein
said molecular unit is phenanthroline, anthracene, benzene, naphthalene, biphenyl, terphenyl, azobenzene, azopyridine, pyridine, bypyridine, bisquinoline, —$C_2H_4$—$X_1$—$C_6H_4$—$X_2$—$C_2H_4$—, or $C_2H_4$—$X_1$—$CH_2$—$C_6H_4$—$CH_2$—$X_2$—$C_2H_4$—, and
$X_1$ and $X_2$ are each O, N, or S, or
said molecular unit is

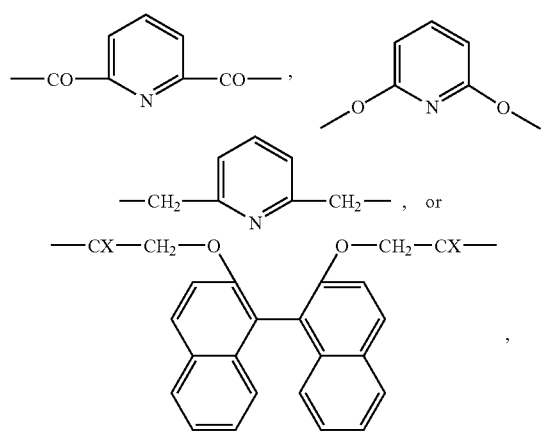

and X is oxygen or hydrogens.

47. The process according to claim 1, wherein the oligonucleotide is an oligodeoxynucleotide modified at its 5' end with an aminohexyl group for binding to said cryptate, and modified at 3' end with a structure containing a maleimide group for binding to the biological molecule.

48. The conjugate according to claim 17, wherein the oligonucleotide is an oligodeoxynucleotide modified at its 5' end with an aminohexyl group for binding to said cryptate, and modified at 3' end with a structure containing a maleimide group for binding to the biological molecule.

49. The process according to claim 1, wherein the oligonucleotide is a thiol-oligonucleotide wherein the thiol function is introduced at the 5' end of the oligonucleotide in the form of a disulfide bond.

50. The conjugate according to claim 17, wherein the oligonucleotide is a thiol-oligonucleotide wherein the thiol function is introduced at the 5' end of the oligonucleotide in the form of a disulfide bond.

51. A fluorescence assay method for detecting an analyte comprising providing a measuring medium containing a sample to be tested for the presence of said analyte, wherein said measuring medium contains at least one fluorescent label, wherein said at least one fluorescent label is a fluorescent conjugate according to claim 17.

* * * * *

UNITED STATES PATENT AND TRADEMARK OFFICE
CERTIFICATE OF CORRECTION

PATENT NO. : 7,309,567 B1  Page 1 of 1
APPLICATION NO. : 09/936563
DATED : December 18, 2007
INVENTOR(S) : Herve Bazin It is certified that error appears in the above-identified patent and that said Letters Patent is hereby corrected as shown below:

Column 18, line 62, reads "R is absence" should read --R is absent--
Column 21, line 28, reads "aryleneis" should read --arylene is--
Column 22, line 15, reads "R is absence" should read --R is absent--
Column 22, line 19-20, reads "and are which" should read --and which--
Column 22, line 28, reads "of a pair molecules" should read --of a pair of molecules--
Column 24, line 45, reads "aryleneis" should read --arylene is--
Column 26, line 3, reads "where in" should read --wherein--
Column 26, line 25, reads "and ©, consists" should read --and © consists--
Column 26, line 61, reads "at 3' end" should read --at its 3' end--
Column 26, line 66, reads "at 3' end" should read --at its 3' end--

Signed and Sealed this

Sixteenth Day of December, 2008

JON W. DUDAS
*Director of the United States Patent and Trademark Office*